(12) United States Patent
Cakmak (10) Patent No.: US 11,141,089 B2
(45) Date of Patent: *Oct. 12, 2021

(54) SYSTEM FOR MONITORING AUDITORY STARTLE RESPONSE

(71) Applicant: Yusuf Ozgur Cakmak, Istanbul (TR)

(72) Inventor: Yusuf Ozgur Cakmak, Istanbul (TR)

( * ) Notice: Subject to any disclaimer, the term of this patent is extended or adjusted under 35 U.S.C. 154(b) by 0 days.

This patent is subject to a terminal disclaimer.

(21) Appl. No.: 16/695,103

(22) Filed: Nov. 25, 2019

(65) Prior Publication Data

US 2020/0100719 A1 Apr. 2, 2020

Related U.S. Application Data

(63) Continuation-in-part of application No. 15/642,287, filed on Jul. 5, 2017, now Pat. No. 10,939,862.

(51) Int. Cl.
*A61B 5/16* (2006.01)
*A61B 5/00* (2006.01)
*A61B 5/389* (2021.01)

(52) U.S. Cl.
CPC ........... *A61B 5/165* (2013.01); *A61B 5/0022* (2013.01); *A61B 5/0077* (2013.01); *A61B 5/162* (2013.01);
(Continued)

(58) Field of Classification Search
CPC ... A61B 5/1103; A61B 5/6815; A61B 5/6898; A61B 5/1104; A61B 5/05; A61B 5/0492;
(Continued)

(56) References Cited

U.S. PATENT DOCUMENTS 4,690,144 A 9/1987 Rise et al.
6,409,655 B1 * 6/2002 Wilson ................. A61M 21/00
600/28
(Continued)

FOREIGN PATENT DOCUMENTS

EP 1671670 A1 6/2006
WO WO2007/136901 A2 11/2007
(Continued)

OTHER PUBLICATIONS

Benning et al., "Emotional modulation of the post-auricular reflex," dated Oct. 13, 2003, pp. 426-432, Psychophysiology 41 (Jun. 2004) Blackwell Publishing Inc., available at https://www.researchgate.net/publication/8602987.
(Continued)

*Primary Examiner* — Matthew Kremer
*Assistant Examiner* — Avery M Foley
(74) *Attorney, Agent, or Firm* — Crowell & Moring LLP (57) ABSTRACT

A diagnostic system for measuring and analyzing startle response of a subject comprises a stimuli delivery circuitry, whereby startle stimuli and prepulse stimuli are delivered to the subject. Said diagnostic system comprises at least one sensor circuitry, whereby the startle response(s) of the subject are detected and recorded. Said sensor circuitry comprises at least one electrode and one eye response measuring system, such as a camera. Said diagnostic system comprises a diagnosis circuitry whereby the features of the startle response(s) and prepulse inhibition of the subject are extracted and analyzed. Said startle response(s) of said subject detected by said sensor circuitry comprise eye response, such as pupillary response and/or eyeblink response, post-auricular muscle response and intrinsic auricular muscle response.

24 Claims, 2 Drawing Sheets

(52) U.S. Cl.
CPC .............. *A61B 5/163* (2017.08); *A61B 5/389* (2021.01); *A61B 5/742* (2013.01)
(58) Field of Classification Search
CPC ..... A61B 5/0024; A61B 5/0022; A61B 5/165; A61B 5/162; A61B 5/163; A61B 5/16; A61B 5/0488; A61B 5/0077; A61B 5/742; A61B 5/382; A61B 5/389; G16H 40/67

See application file for complete search history.

(56) References Cited

U.S. PATENT DOCUMENTS

| | | | |
|---|---|---|---|
| 2008/0249594 A1 | 10/2008 | Dietrich et al. | |
| 2009/0306484 A1 | 12/2009 | Kurtz et al. | |
| 2010/9217348 | 8/2010 | DiLorenzo | |
| 2011/0093049 A1 | 4/2011 | Hinrichsen | |
| 2011/0208265 A1 | 8/2011 | Erickson et al. | |
| 2012/0078323 A1 | 3/2012 | Osorio | |
| 2013/0079862 A1 | 3/2013 | Ellrich | |
| 2013/0123568 A1 | 5/2013 | Hamilton et al. | |
| 2013/0123684 A1 | 5/2013 | Giuffrida et al. | |
| 2014/0065132 A1* | 3/2014 | Hsiao | A61P 1/12 424/130.1 |
| 2015/0289813 A1 | 10/2015 | Lipov | |
| 2016/0106982 A1* | 4/2016 | Cakmak | A61N 1/36067 607/48 |
| 2016/0279435 A1* | 9/2016 | Hyde | A61H 23/02 |
| 2016/0374594 A1* | 12/2016 | Garcia Molina | A61B 3/145 600/558 |
| 2017/0365101 A1* | 12/2017 | Samec | A61B 3/09 |

FOREIGN PATENT DOCUMENTS

| | | | |
|---|---|---|---|
| WO | WO 2010/048261 A1 | 4/2010 | |
| WO | WO2012/129465 A1 | 9/2012 | |
| WO | WO2014/179671 A1 | 11/2014 | |
| WO | WO2015/129465 A1 | 9/2015 | |

OTHER PUBLICATIONS

Braff et al., "Human studies of prepulse inhibition of startle: normal subjects, patient groups, and pharmacological studies," dated Jun. 26, 2001, pp. 234-258, Psychopharmacology 156 (2001).

Chau et al., "Real Time Eye Tracking and Blink Detection with USB Cameras," dated May 12, 2005, pp. 1-11, Boston University Computer Science Technical Report No. 2005-12.

Dichter et al., "Affective Modulation of the Startle Eyeblink and Postauricular Reflexes in Autism Spectrum Disorder," dated Jul. 2010, pp. 858-869, J Autism Dev Disord 40(7) (2010).

Echiverri-Cohen et al., "Analysis of inhibitory functioning in individuals with chronic posttraumatic stress disorder," dated Dec. 20, 2015, pp. 94-103, Elsevier, Journal of Anxiety Disorders 37 (2016).

Freeman et al., "Neural circuitry and plasticity mechanisms underlying delay eyeblink conditioning," dated Aug. 17, 2011, pp. 666-677, Cold Spring Harbor Laboratory Press.

Grillon et al., "A review of the modulation of the startle reflex by affective states and its application in psychiatry," dated May 28, 2003, pp. 1557-1579, Elsevier, National Institute of Mental Health, DHHS, Mood and Anxiety Disorders Program, Clinical Neurophysiology 114 (2003).

Grillon et al., "Baseline startle amplitude and prepulse inhibition in Vietnam veterans with PSTD," Psychiatry Research 64, dated May 5, 1996, pp. 169-178, Elsevier, National Center for Posttraumatic Stress Disorder, Department of Veteran's Affairs Medical Center and Department of Psychiatry, Yale University School of Medicine.

Hess et al., "Postauricular and eyeblink startle responses to facial expressions," dated Jan. 28, 2007, pp. 431-435, Psychophysiology, 44, (2007) Society for Psychophysiological Research, Blackwell Publishing Inc.

Lee et al., "Blink detection robust to various facial poses," dated Aug. 31, 2010, pp. 356-372, Elsevier, Journal of Neuroscience Methods 193 (2010).

Matsuo et al., "Tragicus and Antitragicus Muscles as Constrictors of the External Auditory Meatus," dated 1987, pp. 82-83, European Journal of Plastic Surgery 10 (1987).

O'Beirne et al., "Basic properties of the sound-evoked post-auricular muscle response (PAMR)," dated Aug. 23, 1999, pp. 115-132, Elsevier, Hearing Research 138 (1999).

Shalev et al., "Auditory Startle Response in Trauma Survivors With Posttraumatic Stress Disorder: A Prospective Study," dated Feb. 2000, pp. 255-261, American Journal of Psychiatry 157 (2000).

Zoladz et al., "Current status on behavioral and biological markers of PTSD: A search for clarity in a conflicting literature," dated Mar. 27, 2013, pp. 860-895, Elsevier, Neuroscience and Biobehavioral Reviews 37 (2013).

Mathôt, S., "Pupillometry: Psychology, Physiology, and Function," dated Feb. 20, 2018, pp. 1-23, Journal of Cognition, 1(1): 16, pp. 1-23, DOI: https://doi.org/10.5334/joc.18.

International Search Report of the International Searching Authority, dated Jan. 7, 2014, pp. 1-3, issued in International Application No. PCT/IB2013/055327, European Patent Office, Rijswijk, The Netherlands.

International Preliminary Report on Patentability (PCT Article 36 and Rule 70), dated Mar. 9, 2015, pp. 1-19, issued in International Application No. PCT/IB2013/055327, European Patent Office, Munich, Germany.

Intention to Grant, dated Jun. 13, 2017, pp. 1-46, issued In International Application No. EP 13 762 562.0, European Patent Office, Munich, Germany.

\* cited by examiner

SYSTEM FOR MONITORING AUDITORY STARTLE RESPONSE

RELATED APPLICATIONS

The present patent document is a continuation-in-part of application Ser. No. 15/642,287, filed Jul. 5, 2017, which is hereby incorporated by reference.

TECHNICAL FIELD

The present disclosure relates to a system whereby the auditory startle response of a subject is determined for diagnosis of PTSD.

BACKGROUND

Post-traumatic stress disorder (PTSD) can develop in individuals exposed to intense trauma that threatens physical injury or death. People who develop PTSD endure chronic psychological distress by repeatedly reliving their trauma through intrusive, flashback memories which are frequently precipitated by the presence of cues associated with the traumatic event. Additional debilitating symptoms, such as depression and substance abuse usually occur alongside the re-experiencing and avoidance symptoms of the disorder. Over the decades several physiological and behavioral abnormalities associated with PTSD have been documented, including heightened autonomic arousal, exaggerated startle, abnormally low baseline levels of cortisol, smaller hippocampal volume and cognitive impairments based on impaired hippocampal and prefrontal cortical functioning (Zoladz and Diamond. Neurosci Biobehav Rev. 2013. 37:860-895).

Currently PTSD is diagnosed by heart rate variability, questionnaires such as CAPS-5 and the PTSD checklist and neuroimaging. However, heart rate variability has limited effectiveness and is still controversial while questionnaires are highly subjective and therefore can be unreliable. Neuroimaging methods most widely used to diagnose PTSD are functional magnetic resonance imaging (FMRI) and magnetoencephalography (MEG). Neuroimaging has high accuracy but is very expensive to operate and has limited availability. Therefore, there exists a need for alternative biological diagnostic methods that are practical, accurate and inexpensive.

SUMMARY

The presence of a physiological alteration accompanying a mental disorder, such as PTSD, can produce data that are more objective and more readily quantifiable than self-report data. For this reason, other biological markers, such as exaggerated startle response are potential tools to diagnose PTSD. The startle response is a response to abrupt and intense stimulation, consisting of a rapid sequential muscle contraction with the likely purpose of facilitating the flight reaction and/or to protect the body from sudden attack. The amplitude of startle response is variable in a way that reflects variation in the internal state of the person, such as fear and anxiety, and so the startle reflex can be used as a probe of this internal state (Grillon and Baas. Clin Neurophysiol. 2003. 114:1557-1579).

As mentioned above, exaggerated startle is linked to PTSD and is also a DSM-5 diagnostic criterion for the disorder. The abnormal physiological startle response seen in trauma survivors may develop, along with PTSD, after traumatic exposure as a consequence of a progressive sensitization of the central nervous system (CNS). The exaggerated startle response is generally measured by measurement of eye movement, such as, for example, by recording the eyeblink reflex, cardiac acceleration and increased electrodermal conductivity. The eyeblink consists of a rapid contraction of the orbicularis oculi muscle which is innervated by the facial nerve. The eyeblink startle can be elicited by brief and intense auditory, visual or tactile stimuli with a fast rise time, acoustic startle being the most commonly used. Another example measurement of eye movement to measure exaggerated startle response may be by pupillometry, which is the measurement of pupil size and reactivity. Pupil constriction is controlled by the iris sphincter muscle and pupil dilation is controlled by the iris dilator muscle. The iris sphincter is innervated by the parasympathetic nervous system, the part of the autonomic nervous system that is involved in homeostasis. The iris dilator muscle is controlled by the sympathetic nervous system, the part of the autonomic nervous system that is involved in arousal, wakefulness, and the fight-or-flight response. The dilation pathway is a subcortical pathway that starts at the hypothalamus and the locus coeruleus (LC) and connects to the iris dilator muscle. The pupil dilates after an arousing stimulus, thought, or emotion, for example a visual or acoustic stimulus (Mathôt. Journal of Cognition. 2018. 1:1-23).

Acoustic startle is evoked by short (50 ms) noises, usually broadband or white noise with a high intensity (90-110 dB). Startle stimuli can be delivered at any time to probe ongoing affective and mental processes. Electrical activity associated with contraction of the orbicularis oculi muscle can, for example, be detected with an EMG using two electrodes below one eye (Grillon and Baas. Clin Neurophysiol. 2003. 114:1557-1579; Shalev et al. Am J Psychiatry. 2000. 157: 255-261).

Methods and devices utilizing exaggerated startle response as a tool to assist in diagnosing PTSD are present in the art. An example of such a method may be referred to as WO 2014/179671 (A1), which discloses a system and method for classification and diagnosis of patients suffering from anxiety disorders, such as PTSD, by measuring objective physiological measures, such as inter-heartbeat interval and skin conductance. The system comprises a stimulus delivery module that provides audio and visual, traumatic or non-traumatic stimulus to the subject. The system then measures various resulting physiological signals and extracts features from the physiological measures and a diagnosis is made by classifying the extracted features.

Another example may be referred to as US 2015/289813 (A1), which describes a system and method for the biological diagnosis of PTSD comprising an electronic device equipped with a built-in or attachable camera, built-in or attachable flash or controllable light source, and a software application. The software application includes a method that records and monitors the diameter of an individual's pupil prior to and after the application of light, using the camera and flash in communication with the electronic device. In another embodiment, the method includes the use of emotionally-charged visual stimuli to increase the accuracy of the diagnosis. In still another embodiment, a heart rate monitor is used to monitor the individual's heart rate variability to further increase the accuracy of the diagnosis. In still another embodiment, the method also measures the auditory startle response by measuring the orbicularis oculi response of the individual by electromyography. The method analyzes the data collected and determines the likelihood of individual suffering from PTSD.

An alternative measure of exaggerated startle response is the post-auricular muscle response (PAMR). PAMR is a large sound-evoked vestigial muscle response that acts to pull the ear backward, which can be evoked by clicks or tone-bursts and can be measured on the skin surface over the muscle behind the ear by electrodes. Currently, PAMR is mostly used as a clinical tool to test hearing due to the speed and ease with which the response can be obtained (O'Beirne and Patuzzi. Hearing Res. 1999. 138:115-132).

An example of hearing-related use of PAMR may be referred to as WO 2012/129465 (A1) which discloses an arrangement for custom fitting a hearing prosthesis system, such as cochlear implant systems, to a patient to optimize its operation. The PAMR measurement determines a PAMR of the patient to an auditory stimulus signal. For example, the PAMR may include a PAMR amplitude growth function or a PAMR threshold stimulus level at which a PAMR is measured in the patient. Then a patient fitting module sets an operating characteristic of the hearing prosthesis system based on the PAMR response.

Another example may be referred to as WO 2007/136901 (A2), which discloses a device and method for objectively measuring tinnitus in human and animal subjects. The startle reflex is induced by exposing a subject to an alteration in a sound pattern otherwise qualitatively similar to the subject's tinnitus. The subject's acoustic startle response is obtained and used to determine whether the subject detected the alteration of the sound pattern. The device comprises a controller for selecting a primary sound pattern and selecting a reflex stimulus sound pattern, a generator for generating signals associated with the sound patterns selected by the controller, a transducer for converting the generated signals to the selected sound patterns and exposing the selected sound patterns to the subject and a response sensor for detecting a response by the subject to the selected reflex stimulus sound pattern.

However, recent studies have also shown that patients with PTSD exhibited normal acoustic startle amplitude, but showed a significant reduction in prepulse inhibition (PPI) relative to civilians. PPI occurs when a relatively weak sensory event (prepulse) is presented just before a strong startle inducing stimulus and reduces the magnitude of the startle response (Grillon et al. Psychiatry Res. 1996. 64:169-178). For example eye movement measurement in the form of an eyeblink response is reduced when the subject is shown a pleasant visual, such as a photo of a smiling baby, just before the acoustic startle stimuli is delivered. PPI is thought to occur through a sensorimotor gating system that functions as an attentional filter to protect limited capacity systems from being overloaded with incoming sensory information. Increased PPI is thought to be associated with more effective information processing, whereas reduced PPI is thought to reflect reduced efficiency in inhibiting information. Thus, impaired PPI may reflect a reduced ability to inhibit sensory information and potentially a failure of sensorimotor gating. Studies show reduced PPI in individuals with PTSD. Lower PPI is also associated with higher overall PTSD severity, reexperiencing and hyperarousal symptoms (Echiverri-Cohen et al. J Anxiety Disord. 2016. 37:94-103).

The potentiation of the eyeblink reflex represents activation of the defensive emotional system which promotes withdrawal from frightening or threatening stimuli and is reduced by pleasant stimuli and enhanced by unpleasant stimuli. In contrast, potentiation of PAMR represents activation of the appetitive emotional system, which drives people to approach pleasant or life-sustaining stimuli, which is enhanced by pleasant stimuli and reduced by unpleasant stimuli (Dichter et al. J Autism Dev Disord. 2010. 40:858-869). Therefore, utilizing these two reflexes that show complementary responses to PPI is a useful tool for diagnosing PTSD.

The inventors of the present system have also discovered an additional alternative measure of exaggerated startle response, which is the intrinsic auricular muscle response (IAMR). Intrinsic auricular muscles comprise helicis major, helicis minor, tragicus and antitragicus muscles. It is known that the tragicus and antitragicus muscles cooperate to constrict the external auditory meatus as the orbicularis oculi muscle constricts the palpebral fissure (Matsuo and Hiroshe. Eur J Plast Surg. 1987. 10:82-83). This is thought to be due to the eyeblink pathway wherein eyelid movement is generated by the facial motor nucleus (Freeman and Steinmetz. Learn Mem. 2011. 18:666-677). Facial nerve additionally innervates the muscles of the auricle. As a result, signals for movement of the orbicularis oculi transmitted by the facial nerve while blinking also reach the tragicus and antitragicus muscles, causing the constriction of the external auditory meatus. Therefore it is possible to determine the startle response by measuring the intrinsic auricular muscle response (IAMR) of the subject by electrodes on the skin surface over the muscles. It is also possible to use helicis major, helicis minor muscles for this purpose.

The present disclosure aims to provide a system whereby the acoustic startle reflex, namely eye measurement (such as eyeblink or pupillary response), IAMR and PAMR, of a subject and change in PPI of a subject are measured in order to present an effective and inexpensive method for diagnosing PTSD. The system comprises earphones for delivering auditory stimuli to the subject and a display device, such as a computer screen or a mobile phone for supplying pleasant and/or unpleasant prepulse stimuli to the subject. The earphones additionally contain electrodes for measurement of PAMR and IAMR respectively. The system also contains eye measuring means (such as pupillary response measuring and/or eyeblink measuring systems) for determining the eye response, such as pupillary response and/or eyeblink response, of the subject and measuring the amplitude of the pupillary response and/or the eyeblink response.

The present disclosure provides a diagnostic system as provided by the characterizing features described herein.

An interesting feature relates to a system whereby the acoustic startle reflex of a subject is measured in order to present an effective and inexpensive method for diagnosing PTSD.

Another interesting feature relates to provide a system whereby the lateralization of the pupillary response to stimuli is measured and used as a marker in order to present an effective and inexpensive method for diagnosing PTSD.

Another interesting feature relates to providing a system whereby startle eyeblink response and/or startle pupillary response, along with PAMR and IAMR and change in PPI of a subject are simultaneously measured and analyzed in order to present a corroborative, effective and inexpensive method for diagnosing PTSD.

Another interesting feature relates to providing a system whereby the lateralization of the pupillary response to stimuli is measured and used as a marker in order to present an effective and inexpensive method for determining the possible location of the damage to brain stem pathways.

BRIEF DESCRIPTION OF THE DRAWINGS

Accompanying drawings are given solely for the purpose of exemplifying a diagnostic system, whose advantages were outlined above and will be explained in brief hereinafter.

The drawings are not meant to delimit the scope of protection, nor should they be referred to alone in an effort to interpret the scope without recourse to the technical disclosure in the description.

DETAILED DESCRIPTION

The following numerals are referred to in the detailed description:
10 Subject
11 Pinna
12 Post-auricular muscle
13 Tragicus muscle
14 Antitragicus muscle
15 Eye of subject or orbicularis oculi
16 Pupil
17 Iris sphincter muscle
18 Iris dilator muscle
100 Diagnostic system
110 Stimuli delivery module
111 Sensor module
112 Diagnosis module
120 Startle stimuli
121 Prepulse stimuli
130 eye response (pupillary response or eyeblink response)
131 Post-auricular muscle response
132 Intrinsic auricular muscle response
200 Ear-wearable body
201 Earphones
202 Measurement portion
203 Smartphone
204 Screen
205 Camera Recent studies have demonstrated that the eyeblink response to sudden acoustic startle stimuli is modulated by the emotional state of the individual. When an individual is exposed to an unpleasant stimulus, the relevant subcortical, aversive system circuitry is activated which leads to the augmentation of defensive reflexes such as the eyeblink response reflex. Because appetitive and defensive states are opponent states, the opposite effect can be observed when the individual is exposed to pleasant stimuli. On the other hand, post-auricular muscle reflex (PAMR) displays an opposite pattern. Namely, individuals show an augmented PAMR to an acoustic startle probe when exposed to pleasant stimuli and a reduced one when exposed to unpleasant stimuli (Hess et al. Psychophysiology. 2007. 44:431-435). As PAMR is also evoked by an acoustic probe stimulus, it may be assessed concurrently with the startle eyeblink response.

A recent study has shown that, veterans higher in PTSD reports also showed significantly larger pupils to threatening pictures. Studies have also found increased pupil size to arousing pictures and emotional auditory stimuli. Data from the study suggest increased autonomic arousal in those with higher PTSD symptoms when exposed to threatening stimuli, which is consistent with the clinical presentation of PTSD (Kimble, et al. J Anxiety Disord. 2010. 24:293-299). Another study has shown that individuals with PTSD showed significantly more pupil dilation to threat-relevant stimuli compared to the neutral figural elements, and to trauma-exposed controls. Arousal-related pupil dilation significantly predicted PTSD after time elapsed since trauma, cumulative violence exposure, and trait anxiety were statistically controlled. (Cascardi, et al. J Trauma Stress. 2015. 28:370-374). Therefore, pupillometry can be a valuable addition to the study of dysregulated autonomic arousal after trauma.

As mentioned above, pupil size is determined by a balancing act between two smooth muscles: the sphincter and dilator muscles of the iris. The dilator muscle is innervated by sympathetic neurons in the superior cervical ganglion (SCG), which is, in turn, innervated by the intermediolateral cell column (IML) of the spinal cord. The sphincter muscle is innervated by parasympathetic neurons in the ciliary ganglion (CG), which is, in turn, innervated by the Edinger-Westphal nucleus (EWN). Thus, either excitation of the sympathetic SCG neurons or inhibition of the parasympathetic EWN neurons results in pupil dilation. Studies have shown that unilateral LC stimulation evoked pupil dilation. It was shown that unilateral LC activation evoked bilateral dilation and an across-eye difference in the size of the evoked bilateral dilation, indicating a lateralization in the pathways between the LC and both pupils. It was found that the LC influences the ipsilateral pupil through both parasympathetic and sympathetic pathways but influences the contralateral pupil only through the parasympathetic pathway. Therefore, differences between bilateral pupil dilations were mainly attributed to sympathetic contribution, suggesting that a measurement of across-eye differences in bilateral pupil dilation may present itself as a biomarker for abnormal autonomic activities (Liu, et al. Cell Reports. 2017. 20:3099-3112.). A recent study has also shown that there is a link between LC hyperactivity and PTSD (Naegeli, Christoph, et al. Biol Psychiatry. 2018. 83:254-262).

Therefore, the lateralization of the pupillary response can be used as a marker for the diagnosis of PTSD. Alternatively, the lateralization of the pupillary response can be used to determine the possible location of the damage to brain stem pathways.

When an individual is exposed to an unpleasant stimulus, the relevant subcortical, aversive system circuitry is activated which leads to the augmentation of responses such as the eyeblink response, pupillary response, skin conductance responses and other startle response described above.

The pupillary response can start emerging as early as 200 ms after stimulus onset and is modulated by arousal: the pupil has been shown to dilate more strongly in response to emotionally arousing picture stimuli as well as to arousing sounds in comparison to neutral stimuli. The conditioned pupil response is often defined as the increase in diameter from stimulus onset to offset, spanning several seconds. Besides responding to arousal, the pupil has been shown to be sensitive to a variety of higher-order cognitive processes such as error monitoring, uncertainty, or cognitive load. It is yet unknown how pupil responses relate to other physiological readouts of conditioned fear like startle responses (Leuchs, Schneider and Spoormaker. Psychophysiology. 2019. 56:e13283). Therefore an additional advantage of the present system is correlating known modes of startle responses such as PAMR and IAMR with pupillary response.

The magnitude of startle responses and/or eyeblink responses are modified if the startle-eliciting noise is preceded by the occurrence of a transient stimulus, an effect known as prepulse inhibition (PPI). PPI is thought to reflect a low-level sensory gating mechanism by which excess or trivial stimuli are screened or "gated out" of awareness, so that an individual can focus attention on the most salient aspects of the stimulus-laden environment. PPI is a ubiquitous phenomenon and can occur when the prepulse and startling stimuli are in the same or different sensory modalities (Benning et al. Psychophysiology 2004. 41:426-432; Braff et al. Psychopharmacology. 2001. 156:234-258).

Patients with PTSD exhibit normal acoustic startle amplitude, but show a reduction in PPI relative to the non-affected subjects. PPI deficits are associated with perceptual abnormalities and deficiencies in gating irrelevant thoughts. Patients with PTSD are also characterized by perceptual deficits and by an inability to gate intrusive thoughts. Some of the symptoms of PTSD such as the intrusion of unwanted thoughts (e.g. flashback) could be hypothesized to result from a gating deficit. Alternatively, reduced PPI in patients with PTSD can reflect an attentional deficit. PPI is increased with increased attention to the prepulse and reduced PPI in patients with PTSD suggests less processing of the prepulse, perhaps because of distraction by internal stimuli (e.g. thoughts) (Grillon et al. Psychiatry Res. 1996. 64:169-178).

Figure 1A:
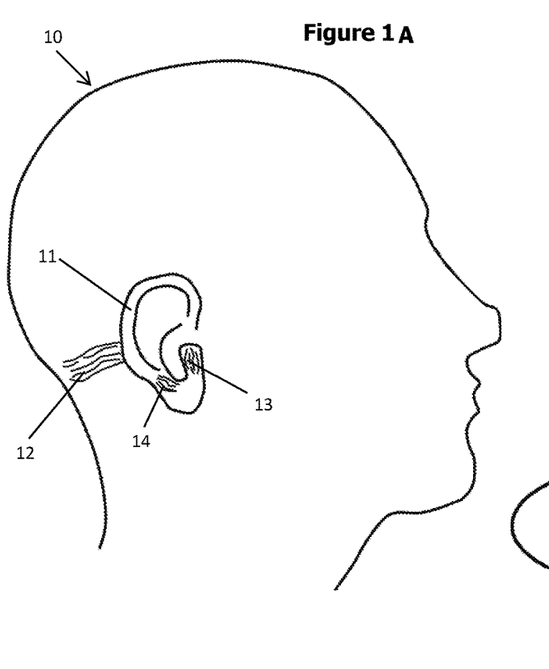
FIG. 1A and FIG. 1B demonstrate anatomical structures of the human head relevant to the present system.
Figure 1B:
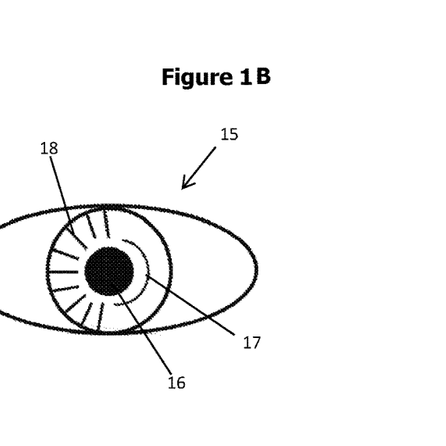
Figure 2:
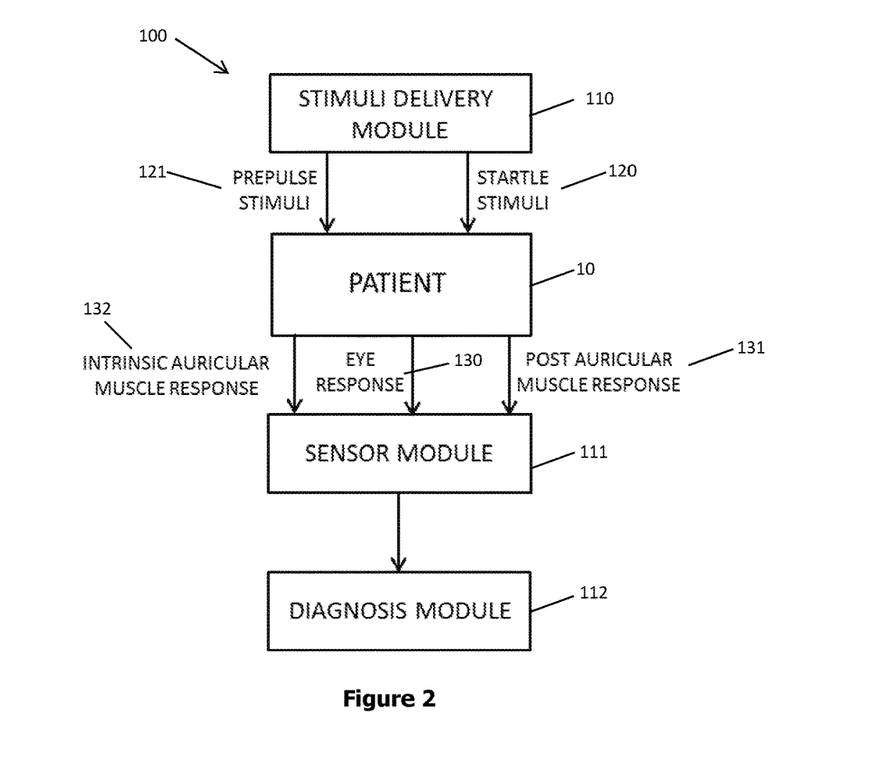
FIG. 2 demonstrates a block diagram of a diagnostic system.

The present disclosure discloses a diagnostic system (100) comprising a stimuli delivery module (110), connected to earphones and at least one display, whereby startle stimuli (120) and prepulse stimuli (121) are delivered to subject (10); at least one sensor module (111), connected to at least one electrode and one eye response measuring means, such as pupillary response measuring system and/or eyeblink response measuring system, whereby the startle response, i.e. the eye response (pupillary response and/or eyeblink response) (130), PAMR (131) and IAMR (132), and PPI of subject (10) are detected and recorded; and a diagnosis module (112) whereby the features of the startle response and PPI of subject (10) are extracted and classified by a software application (not shown) as will be delineated hereinafter (FIG. 1A, FIG. 1B and FIG. 2).

As mentioned above and herein with reference to FIG. 1A, FIG. 1B and FIG. 2, PAMR (131) is a large and simply measured auditory response, (up to 8 kHz or higher). The response is optimally recorded as the potential difference between the skin overlying the post-auricular muscle (12) and the rear of the pinna (11) of the subject (10), with a bandwidth from 10 to 300 Hz. This electrode positioning also reduces background electrical interference and muscle activity and eliminates blink artefacts (O'Beirne and Patuzzi. Hearing Res. 1999. 138:115-132).

As also mentioned above, IAMR (132) can be used as an alternative measure of exaggerated startle response. The response can be recorded by placing electrodes on the tragicus (13) and antitragicus muscles (14) of the subject (10). In an example, simultaneous measurement of eyeblink response (130) and IAMR (132) allows for the eyeblink data and IAM data to be correlated in order to generate an index to determine the relationship between eyeblink response (130) and IAMR (132). The index compiled from the correlation of eyeblink and IAM data may also have the advantage of providing noise reduction in startle response measurements. In an alternative embodiment, IAMR (132) can be recorded by placing electrodes on the helicis major, helicis minor of the subject (10).

The diagnostic system (100) measures the auditory startle response (130, 131, 132) of a subject (10). Auditory startle response (130, 131, 132) is measured by stimuli delivery module (110) by delivering startle stimuli (120) to subject (10). Startle stimuli (120) are delivered by playing a sudden, loud tone or noise, such as a sound burst of 95 decibels, for subject (10) preferably using earphones. The diagnostic system (100) additionally measures the PPI of a subject (10) by delivering prepulse stimuli (121) to a subject (10) shortly before delivering startle stimuli (120). Prepulse stimuli (121) are delivered by showing pleasant, unpleasant and neutral visuals to subject (10) via a display. Display includes monitors, TV screens, flat panel displays, video walls, or any other type of display device to display the prepulse stimuli (121) to subject (10). In one embodiment, visuals are selected from the International Affective Picture System (ZAPS) to represent the different valence (pleasant, unpleasant and neutral) categories. Preferably, startle stimuli (120) is delivered to the subject (10) 3-5 s after the delivery of prepulse stimuli (121).

The system may make use of the lateralization of eye response (130), such as pupillary response, as a biomarker for the diagnosis of PTSD. In a preferred embodiment, startle stimuli (120) is delivered unilaterally using earphones. Namely, startle stimuli (120) is delivered via the right ear or left ear and the bilateral eye response (130), such as pupillary response, is monitored. Alternatively, the system may make use of the lateralization of eye response (130), such as pupillary response, as a biomarker for damages to the brain stem of a subject. By measuring the difference in the ipsilateral and contralateral response to startle stimuli (120) in each eye, the possible location of the damage to brain stem pathways may be assessed.

Diagnostic system (100) also includes a sensor module (111) comprising plurality of sensors (not shown). The sensors are circuitry configured to monitor and record a plurality of different physiological responses to subject's (10) exposure to stimuli output (120, 121), such as eye response (130), such as pupillary and/or eyeblink, PAMR (131) and IAMR (132). The physiological response data are collected during the subject's (10) exposure to the stimuli.

Sensor module (111) detects the subject's (10) response to startle stimuli (120) by monitoring the subject's (10) eye movement. For example, the eye movement may be eyelid movement and/or movement of muscles associated with eyelid movement (eye response (130)). In embodiments, sensor module (111) detects eye response (130) in the form of eyeblinks by recording such an eye response (130) of the subject (10) with measuring system, such as a camera, and measuring its speed and amplitude through displacement analysis. This can be achieved by any method present in the art, such as the blink detection methods developed by Lee et al. (J Neurosci Methods. 2010. 193:356-372), Chau and Betke (Tech. Rep. 2005-12, Boston University Computer Science) or other methods known to the skilled person. Alternatively, or in addition, the eye movement may by pupillary response (eye response (130)). The monitoring of pupillary response may be achieved by eye movement measuring system utilizing any method present in the art, such as a camera or a desktop mounted eye-tracking system, such as Eyelink-1000 (SR research, Kanata, Ontario, Canada).

Sensor module (111) also comprises at least one electrode designed to be placed on the back of the ear corresponding to post-auricular muscle (12) to measure the PAMR (131) of subject (10) simultaneously while measuring the eye response (130), thereby increasing accuracy. Preferably, sensor module (111) comprises two electrodes to be placed one on the back of the ear of subject (10) directly over post-auricular muscle (12) and one directly adjacent on pinna (11) of subject (10) and a grounding electrode to be placed elsewhere on subject's (10) head. The PAMR (131)

may be determined on one side, either ipsilateral or contralateral, of the subject (10), or on both sides of the subject (10).

Additionally, sensor module (111) comprises a sensor such as an EMG sensor, which detects the electric potential generated by the tragicus muscle (13) and antitragicus muscle (14) in order to measure the IAMR (132) of the subject. The sensor may comprise surface electrodes (surface EMG) or needle-shaped electrodes (intramuscular EMG). In one embodiment, needle-shaped electrodes are pricked on the auricular skin and reaches said tragicus muscle (13) and antitragicus muscle (14).

The eye response (130) (pupillary response and/or eyeblink response), PAMR (131), IAMR (132) and PPI data are collected by sensor module (111) and transmitted to diagnosis module (112). Diagnosis module (112) can be in wired or wireless communication with sensor module (111). Diagnosis module (112) comprises a software application for analyzing data which can include the amplitude and speed of response (130, 131, 132) and change in PPI to determine whether the individual is suffering from PTSD. Alternatively, diagnosis module (112) comprises a software application for analyzing data including the amplitude and speed of eye response (130) of a subject to determine the possible location of the damage to brain stem pathways of said subject.

Diagnosis module (112) may also determine a threshold value depending on at least one of the age, ethnic background, sex and baseline response of subject (10). In some embodiments, diagnosis module (112) combines and applies weights to the processed extracted features and compares the combined value to the threshold. The weighted features can be combined by any arithmetic process. In such embodiments, diagnosis module (110) identifies subject (10) as having PTSD if the combined value is above the threshold, and not having PTSD if the combined value is below the threshold.

In some embodiments, diagnostic system (100) may be coupled to a network interface configured for wired or wireless data communications, and the results may be transmitted to a remote computing system over a computer network and displayed to a clinician, care provider and/or subject (10) by outputting the results via a display device concurrently or after the fact.

In some embodiments, diagnostic system (100) can comprise a mobile electronic device, such as a smartphone, tablet, PC computer or any other like device known in the art.

Diagnostic system (100) allows startle response (130, 131, 132) and PPI to be monitored over time (long-term monitoring) and also emotional state of the subject (10) at that moment to be determined.

Figure 3:
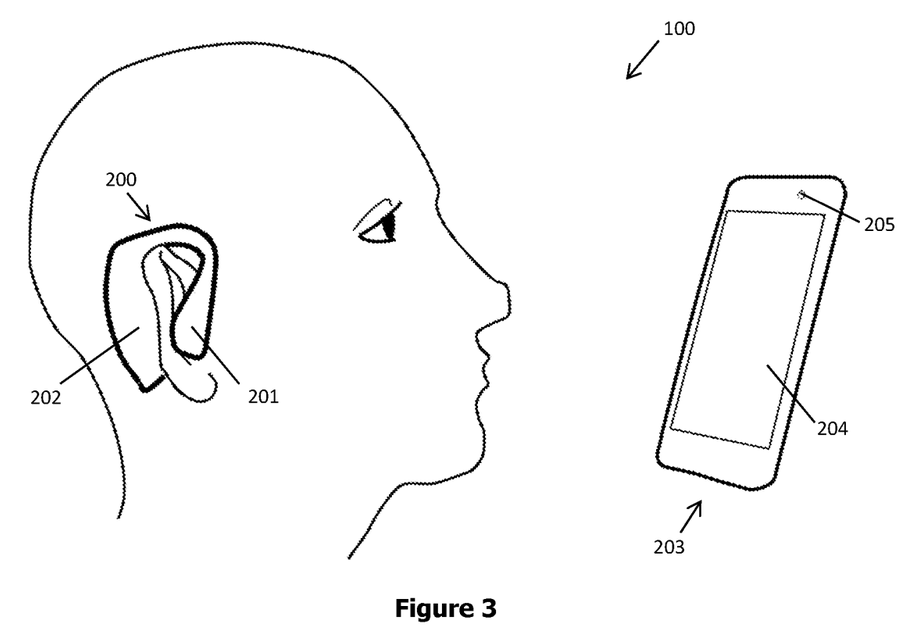
FIG. 3 demonstrates a schematic view of one embodiment of a diagnostic system.

FIG. 3 illustrates an embodiment of diagnostic system (100). Diagnostic system (100) comprises an ear-wearable body (200) equipped with earphones (201) and a measurement portion (202) and a smartphone (203) equipped with a screen (204) and a built-in camera (205) a mobile application (not shown) for the analysis of data.

Earphones (201) are used to deliver startle stimuli (120) to subject (10) and screen (204) is used to deliver prepulse stimuli (121) to subject (10). In alternative embodiments, display may be the screen (204) of a smartphone or other mobile device, tablet, computer.

Measurement portion (202) comprises electrodes designed to be placed on the skin of the back of the ear of subject (10) corresponding to the post-auricular muscle (12) whereby the detection of the PAMR (131) of the subject (10) is realized as described above. Measurement portion (202) additionally comprises electrodes designed to be placed on the skin of the entrance of the ear canal of subject (10) corresponding to the tragicus muscle (13) and antitragicus muscle (14) the detection of the IAMR (132) of the subject (10) is realized.

Camera (205) is used to record the eye movement such as pupil size and/or eyeblink of subject (10) to determine the eye response (130) to startle stimuli (120).

In one aspect, a diagnostic system (100) for measuring and analyzing startle response of a subject (10) is proposed.

In a further aspect, said diagnostic system (100) comprises a stimuli delivery module (110), which is circuitry, whereby startle stimuli (120) and prepulse stimuli (121) are delivered to subject (10).

In a further aspect, said diagnostic system (100) comprises at least one sensor module (111), which is circuitry, whereby the startle response (130, 131, 132) of subject (10) are detected and recorded.

In a further aspect, said sensor module (111) comprises at least one electrode and one pupillary response measuring system and/or one eyeblink response measuring system.

In a further aspect, said diagnostic system (100) comprises a diagnosis module (112), which is circuitry, whereby the features of the startle response (130, 131, 132) and prepulse inhibition of subject (10) are extracted and analyzed.

In a further aspect, said startle response of subject (10) detected by said sensor module (111) comprises eye response (130), post-auricular muscle response (131) and intrinsic auricular muscle response (132).

In a further aspect, said stimuli delivery module (110) comprises a set of earphones whereby startle stimuli (120) is delivered to subject (10).

In a further aspect, said stimuli delivery module (110) comprises a set of earphones whereby startle stimuli (120) is delivered to subject (10) unilaterally.

In a further aspect, said sensor module (111) comprises a pupillary response measuring system whereby the measurement of an eye response (130) such as ipsilateral and contralateral pupillary response to unilateral startle stimuli (120) is facilitated.

In a further aspect, said startle stimuli (120) is a sudden, loud tone or noise.

In a further aspect, said startle stimuli (120) is a sound burst of 95 decibels.

In a further aspect, stimuli delivery module (110) comprises a display whereby prepulse stimuli (121) is delivered to subject (10).

In a further aspect, said prepulse stimuli (120) are pleasant, unpleasant and neutral visuals.

In a further aspect, said prepulse stimuli (120) are pleasant, unpleasant and neutral visuals selected from the International Affective Picture System (ZAPS).

In a further aspect, said sensor module (111) comprises at least one electrode configured to be placed over tragicus (13) and antitragicus muscles (14) of subject (10) whereby measurement of intrinsic auricular muscle response (132) of subject (10) is facilitated.

In a further aspect, said sensor module (111) comprises at least one electrode configured to be placed over helicis major and helicis minor of subject (10) whereby measurement of intrinsic auricular muscle response (132) of subject (10) is facilitated.

In a further aspect, said sensor module (111) comprises at least one electrode configured to be placed on the scalp behind the ear of subject (10) whereby measurement of post-auricular muscle response (131) of subject (10) is facilitated.

In a further aspect, said sensor module (111) comprises one electrode configured to be placed on the back of the ear of subject (10) directly over post-auricular muscle (12) and one electrode configured to be placed directly adjacent on pinna (11) of subject (10).

In a further aspect, said sensor module (111) comprises a grounding electrode.

In a further aspect, an eye response measuring means is an eye response measuring system, such as a camera, whereby measurement of eye response (130) in the form of pupillary response and/or eyeblink of subject (10) is facilitated.

In a further aspect, said sensor module (11) and said diagnosis module (112) are in wired or wireless communication.

In a further aspect, said diagnosis module (112) comprises a software application.

In a further aspect, said diagnosis module (112) comprises a software application whereby feature extraction and analysis of startle response (130, 131, 132) data is performed.

In a further aspect, said startle response (130, 131, 132) data comprises the amplitude and speed of response (130, 131, 132) and change in prepulse inhibition.

In a further aspect, said startle response (130, 131, 132) data comprises the lateralization of pupillary response (130) to unilaterally applied startle stimuli (120).

In a further aspect, said diagnostic system (100) is in wired or wireless communication with a network interface whereby said feature extraction and analysis results are communicated to a clinician, care provider and/or subject (10).

In a further aspect, said diagnostic system (100) is in wired or wireless communication with a network interface whereby said feature extraction and analysis results are outputted via a display device concurrently or after the fact.

In a further aspect, said diagnostic system (100) comprises a mobile electronic device, such as a smartphone, tablet or PC computer.

The methods, devices, processing, circuitry, and logic described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

The subject-matter of the disclosure relates, among others, to the following aspects:

1) A diagnostic system (100) for measuring and analyzing startle response of a subject (10) characterized in that;
    said diagnostic system (100) comprises a stimuli delivery module (110), whereby startle stimuli (120) and prepulse stimuli (121) are delivered to subject (10);
    said diagnostic system (100) comprises at least one sensor module (111), whereby the startle response (130, 131, 132) of subject (10) are detected and recorded;
    said sensor module (111) comprises at least one electrode and one pupillary response measuring means;
    said diagnostic system (100) comprises a diagnosis module (112) whereby the features of the startle response (130, 131, 132) and prepulse inhibition of subject (10) are extracted and analyzed; and
    said startle response of subject (10) detected by said sensor module (111) comprise pupillary response and/or eyeblink response (130), post-auricular muscle response (131) and intrinsic auricular muscle response (132).

2) A diagnostic system (100) as set forth in aspect 1, characterized in that said stimuli delivery module (110) comprises a set of earphones whereby startle stimuli (120) is delivered to subject (10).

3) A diagnostic system (100) as set forth in aspect 2, characterized in that said stimuli delivery module (110) comprises a set of earphones whereby startle stimuli (120) is delivered to subject (10) unilaterally.

4) A diagnostic system (100) as set forth in aspect 3, characterized in that said sensor module (111) comprises a pupillary response measuring means whereby the measurement of ipsilateral and contralateral pupillary response (130) to unilateral startle stimuli (120) is facilitated.

5) A diagnostic system (100) as set forth in aspect 1, characterized in that said startle stimuli (120) is a sudden, loud tone or noise.

6) A diagnostic system (100) as set forth in aspect 5, characterized in that said startle stimuli (120) is a sound burst of 95 decibels.

7) A diagnostic system (100) as set forth in aspect 1, characterized in that stimuli delivery module (110) comprises a display whereby prepulse stimuli (121) is delivered to subject (10).

8) A diagnostic system (100) as set forth in aspect 1, characterized in that said prepulse stimuli (120) are pleasant, unpleasant and neutral visuals.

9) A diagnostic system (100) as set forth in aspect 8, characterized in that said prepulse stimuli (120) are pleasant, unpleasant and neutral visuals selected from the International Affective Picture System (TAPS).

10) A diagnostic system (100) as set forth in aspect 1, characterized in that said sensor module (111) comprises at least one electrode configured to be placed over tragicus (13) and antitragicus muscles (14) of subject (10) whereby measurement of intrinsic auricular muscle response (132) of subject (10) is facilitated.

11) A diagnostic system (100) as set forth in aspect 1, characterized in that said sensor module (111) comprises at least one electrode configured to be placed over helicis major and helicis minor of subject (10) whereby measurement of intrinsic auricular muscle response (132) of subject (10) is facilitated.

12) A diagnostic system (100) as set forth in aspect 1, characterized in that said sensor module (111) comprises at least one electrode configured to be placed on the scalp behind the ear of subject (10) whereby measurement of post-auricular muscle response (131) of subject (10) is facilitated.

13) A diagnostic system (100) as set forth in aspect 12, characterized in that said sensor module (111) comprises one electrode configured to be placed on the back of the ear of subject (10) directly over post-auricular muscle (12) and one electrode configured to be placed directly adjacent on pinna (11) of subject (10).

14) A diagnostic system (100) as set forth in aspect 12, characterized in that said sensor module (111) comprises a grounding electrode.

15) A diagnostic system (100) as set forth in aspect 1, characterized in that said pupillary response and/or said eyeblink response measuring means is a camera whereby measurement of pupillary response and/or eyeblink response (130) of subject (10) is facilitated.

16) A diagnostic system (100) as set forth in aspect 1, characterized in that said sensor module (11) and said diagnosis module (112) are in wired or wireless communication.

17) A diagnostic system (100) as set forth in aspect 16, characterized in that said diagnosis module (112) comprises a software application.

18) A diagnostic system (100) as set forth in aspect 17, characterized in that said diagnosis module (112) comprises a software application whereby feature extraction and analysis of startle response (130, 131, 132) data is performed.

19) A diagnostic system (100) as set forth in aspect 18, characterized in that said startle response (130, 131, 132) data comprises the amplitude and speed of response (130, 131, 132) and change in prepulse inhibition.

20) A diagnostic system (100) as set forth in aspect 3 or 18, characterized in that said startle response (130, 131, 132) data comprises the lateralization of pupillary response (130) to unilaterally applied startle stimuli (120).

21) A diagnostic system (100) as set forth in aspect 18, characterized in that said diagnostic system (100) is in wired or wireless communication with a network interface whereby said feature extraction and analysis results are communicated to a clinician, care provider and/or subject (10).

22) A diagnostic system (100) as set forth in aspect 18, characterized in that said diagnostic system (100) is in wired or wireless communication with a network interface whereby said feature extraction and analysis results are outputted via a display device concurrently or after the fact.

23) A diagnostic system (100) as set forth in aspect 16, characterized in that said diagnosis module (112) comprises a software application whereby correlation of eyeblink response (130) and intrinsic auricular muscle response (132) data is effectuated in order to generate an index to determine the relationship between eyeblink response (130) and intrinsic auricular muscle response (132).

24) A diagnostic system (100) as set forth in any preceding aspect, characterized in that said diagnostic system (100) comprises a mobile electronic device, such as a smartphone, tablet or PC computer.

Various implementations have been specifically described. However, many other implementations are also possible.

The invention claimed is:

1. A diagnostic system for measuring and analyzing a startle response of a subject comprising: a stimuli delivery circuitry configured to deliver startle stimuli and prepulse stimuli to the subject; at least one sensor circuitry configured to detect and record the startle response of said subject; said sensor circuitry comprises at least one electrode and at least one eye response measuring system; a diagnosis circuitry configured to extract and analyze a plurality of features of the startle response and prepulse inhibition of said subject to diagnose post-traumatic stress disorder (PTSD); and said features of said startle response of said subject detected by said sensor circuitry comprising: a pupillary response, a post-auricular muscle response, and an intrinsic auricular muscle response.

2. The diagnostic system as set forth in claim 1, wherein said stimuli delivery circuitry comprises a set of earphones by which said startle stimuli is delivered to said subject.

3. The diagnostic system as set forth in claim 1, wherein said stimuli delivery circuitry comprises a set of earphones through which said startle stimuli is delivered to said subject unilaterally.

4. The diagnostic system as set forth in claim 3, wherein the eye response measuring system is configured to measure as the pupillary response measurement of ipsilateral and contralateral pupillary response to said unilateral startle stimuli.

5. The diagnostic system as set forth in claim 1, wherein said startle stimuli is a sudden, loud tone or noise.

6. The diagnostic system as set forth in claim 5, wherein said startle stimuli is a sound burst of 95 decibels.

7. The diagnostic system as set forth in claim 1, wherein said stimuli delivery circuitry comprises a display in which said prepulse stimuli is delivered to said subject.

8. The diagnostic system as set forth in claim 1, wherein said prepulse stimuli are pleasant, unpleasant and neutral visuals.

9. The diagnostic system as set forth in claim 8, wherein said prepulse stimuli are said pleasant, unpleasant and neutral visuals selected from an International Affective Picture System (ZAPS).

10. The diagnostic system as set forth in claim 1, wherein said at least one electrode is configured to be placed over tragicus and antitragicus muscles of said subject.

11. The diagnostic system as set forth in claim 1, wherein said at least one electrode is configured to be placed over helicis major and helicis minor of said subject.

12. The diagnostic system as set forth in claim 1, wherein said at least one electrode is configured to be placed on a scalp behind an ear of said subject.

13. The diagnostic system as set forth in claim 12, wherein a first electrode of said at least one electrode is configured to be placed on the back of the ear of said subject directly over a post-auricular muscle, and a second electrode of the at least one electrode is configured to be placed on a pinna of said subject.

14. The diagnostic system as set forth in claim 12, wherein said sensor circuitry comprises a grounding electrode.

15. The diagnostic system as set forth in claim 1, wherein said eye response measuring system comprises a camera.

16. The diagnostic system as set forth in claim 1, wherein said sensor circuitry and said diagnosis circuitry are in wired or wireless communication with each other.

17. The diagnostic system as set forth in claim 16, wherein said diagnosis circuitry comprises a software application.

18. The diagnostic system as set forth in claim 17, wherein said software application is stored in memory and executable with a processor circuitry to perform the feature extraction and the analysis of said startle response.

19. The diagnostic system as set forth in claim 18, wherein said startle response comprises an amplitude and speed of response.

20. The diagnostic system as set forth in claim 18, wherein said startle response comprises lateralization of said pupillary response to said startle stimuli.

21. The diagnostic system as set forth in claim 18, wherein said diagnostic system is in wired or wireless communication with a network interface, the network interface configured to communicate said feature extraction and analysis results to a clinician, care provider and/or said subject via said network interface.

22. The diagnostic system as set forth in claim 18, wherein said diagnostic system is in wired or wireless communication with a network interface, and wherein said diagnostic system further comprises a display device to output said feature extraction and analysis results concurrently or after said feature extraction and analysis.

23. The diagnostic system as set forth in claim 18, wherein said diagnostic system comprises a mobile electronic device.

24. A method comprising: delivering, with a stimuli delivery circuitry startle stimuli and prepulse stimuli to a subject; detecting and recording, using at least one sensor circuitry, a startle response of said subject, wherein said sensor circuitry comprises at least one electrode and at least one eye response measurement system; and extracting and analyzing, with a diagnosis circuitry, a plurality of features of the startle response and prepulse inhibition of said subject to diagnose post-traumatic stress disorder (PTSD), wherein said features of said startle response of said subject detected by said sensor circuitry comprise: a pupillary response, a post-auricular muscle response, and an intrinsic auricular muscle response.

\* \* \* \* \*